(12) United States Patent
Conlan et al.

(10) Patent No.: US 11,234,729 B2
(45) Date of Patent: Feb. 1, 2022

(54) MICRO-LIPO NEEDLE DEVICES AND USE THEREOF

(71) Applicant: Aurastem LLC, Solana Beach, CA (US)

(72) Inventors: Bradford A. Conlan, Solana Beach, CA (US); Lucas Fornace, Encinitas, CA (US)

(73) Assignee: AURASTEM LLC, Solana Beach, CA (US)

( * ) Notice: Subject to any disclaimer, the term of this patent is extended or adjusted under 35 U.S.C. 154(b) by 548 days.

(21) Appl. No.: 16/164,183

(22) Filed: Oct. 18, 2018

(65) Prior Publication Data

US 2019/0046231 A1 Feb. 14, 2019

Related U.S. Application Data

(63) Continuation-in-part of application No. PCT/US2017/030247, filed on Apr. 28, 2017.

(51) Int. Cl.

| A61B 17/34 | (2006.01) |
|---|---|
| A61B 18/00 | (2006.01) |
| A61M 1/00 | (2006.01) |
| A61B 17/00 | (2006.01) |
| A61B 17/30 | (2006.01) |

(52) U.S. Cl.
CPC .......... *A61B 17/34* (2013.01); *A61B 17/3403* (2013.01); *A61B 18/00* (2013.01); *A61M 1/79* (2021.05); *A61M 1/84* (2021.05); *A61M 1/88* (2021.05); *A61B 2017/00526* (2013.01); *A61B 2017/00792* (2013.01); *A61B 2017/00969* (2013.01); *A61B 2017/306* (2013.01); *A61B 2017/3407* (2013.01); *A61B 2018/00464* (2013.01); *A61B 2217/005* (2013.01); *A61M 2202/08* (2013.01); *A61M 2205/0244* (2013.01)

(58) Field of Classification Search
CPC ..... A61B 17/34; A61B 18/00; A61B 17/3403; A61B 2018/00464; A61B 2017/3407; A61B 2017/00792; A61B 2017/306; A61M 2202/08
See application file for complete search history.

(56) References Cited

U.S. PATENT DOCUMENTS

| 3,840,008 A * | 10/1974 | Noiles ................. A61M 5/3286 |
|---|---|---|
| | | 604/506 |
| 4,713,053 A | 12/1987 | Lee |
| 5,002,538 A | 3/1991 | Johnson |

(Continued)

FOREIGN PATENT DOCUMENTS

| AU | 2004240645 | 12/2004 |
|---|---|---|
| EP | 2404547 | 1/2012 |

(Continued)

OTHER PUBLICATIONS

Bradford, Conlan; Extended European Search Report for Application No. 17907962.9, filed Nov. 25, 2019, dated Nov. 12, 2020, 8 pages.

(Continued)

*Primary Examiner* — Adam Marcetich
(74) *Attorney, Agent, or Firm* — Fish & Richardson P.C.

(57) ABSTRACT

Embodiments of the present invention disclose micro-lipo needle device and methods of making and using the same.

15 Claims, 9 Drawing Sheets

(56) References Cited

U.S. PATENT DOCUMENTS

| | | | |
|---|---|---|---|
| 5,744,360 A | 4/1998 | Hu et al. | |
| 5,817,050 A | 10/1998 | Klein | |
| 5,911,700 A | 6/1999 | Mozsary et al. | |
| 5,968,008 A | 10/1999 | Grams | |
| 6,020,196 A | 2/2000 | Hu et al. | |
| 6,261,310 B1* | 7/2001 | Neuberger | A61B 18/20 600/21 |
| 7,390,484 B2 | 6/2008 | Fraser et al. | |
| 7,608,048 B2 | 10/2009 | Goldenberg | |
| 7,841,991 B2 | 11/2010 | Douglas et al. | |
| 7,914,504 B2 | 3/2011 | Klein | |
| 8,202,493 B2 | 6/2012 | Buss | |
| 8,489,172 B2 | 7/2013 | Gelbart et al. | |
| 8,652,123 B2 | 2/2014 | Gurtner et al. | |
| 9,133,431 B2 | 9/2015 | Peterson et al. | |
| 10,183,101 B2 | 1/2019 | Conlan et al. | |
| 10,188,777 B2 | 1/2019 | Conlan et al. | |
| 2002/0151874 A1 | 10/2002 | Kolster et al. | |
| 2002/0169469 A1 | 11/2002 | Klein | |
| 2003/0167053 A1 | 9/2003 | Taufig | |
| 2004/0044331 A1 | 3/2004 | Klein | |
| 2005/0025755 A1 | 2/2005 | Hedrick et al. | |
| 2005/0054947 A1* | 3/2005 | Goldenberg | A61B 10/0266 600/567 |
| 2005/0131439 A1* | 6/2005 | Brett | A61B 17/3478 606/170 |
| 2005/0256536 A1* | 11/2005 | Grundeman | A61B 17/11 606/185 |
| 2006/0079921 A1* | 4/2006 | Nezhat | A61B 17/3403 606/185 |
| 2006/0293722 A1* | 12/2006 | Slatkine | A61H 9/0057 607/46 |
| 2007/0010810 A1* | 1/2007 | Kochamba | A61M 5/14248 606/41 |
| 2007/0055179 A1 | 3/2007 | Deem et al. | |
| 2007/0100277 A1 | 5/2007 | Shippert | |
| 2007/0225686 A1 | 9/2007 | Shippert | |
| 2007/0270710 A1 | 11/2007 | Frass et al. | |
| 2007/0270745 A1 | 11/2007 | Nezhat et al. | |
| 2008/0051730 A1* | 2/2008 | Bikovsky | A61M 5/14248 604/240 |
| 2008/0058851 A1* | 3/2008 | Edelstein | A61B 17/3415 606/185 |
| 2008/0154240 A1 | 6/2008 | Shippert | |
| 2008/0275473 A1* | 11/2008 | Filipi | A61B 17/0625 606/145 |
| 2009/0088823 A1* | 4/2009 | Barak | A61B 18/203 607/89 |
| 2010/0057056 A1 | 3/2010 | Gurtner et al. | |
| 2010/0125240 A1 | 5/2010 | Spedden et al. | |
| 2010/0137841 A1 | 6/2010 | Khouri et al. | |
| 2010/0228182 A1* | 9/2010 | Clark, III | A61B 18/20 604/21 |
| 2010/0228207 A1* | 9/2010 | Ballakur | A61B 17/00234 604/319 |
| 2010/0318070 A1 | 12/2010 | Mitra et al. | |
| 2011/0166509 A1* | 7/2011 | Gross | A61M 5/425 604/60 |
| 2012/0027804 A1 | 2/2012 | Odermatt et al. | |
| 2012/0165725 A1 | 6/2012 | Chomas et al. | |
| 2012/0259311 A1 | 10/2012 | Hirshberg | |
| 2014/0155869 A1 | 6/2014 | Seare | |
| 2014/0257272 A1* | 9/2014 | Clark, III | A61M 37/00 606/37 |
| 2015/0289858 A1 | 10/2015 | McGillicuddy et al. | |
| 2015/0352266 A1 | 12/2015 | Gourlay | |
| 2015/0374888 A1 | 12/2015 | Shippert | |
| 2016/0058924 A1 | 3/2016 | Kim | |
| 2016/0106889 A1* | 4/2016 | Conlan | A61M 1/0001 604/319 |
| 2017/0021066 A1* | 1/2017 | Sforza | A61M 1/008 |
| 2017/0049942 A1 | 2/2017 | Conlan | |
| 2017/0049972 A1* | 2/2017 | Persons | A61M 5/3297 |
| 2017/0203040 A1 | 7/2017 | Conlan | |
| 2017/0303956 A1* | 10/2017 | Misle | A61M 25/0612 |
| 2017/0368226 A1 | 12/2017 | Pilkington et al. | |
| 2018/0117263 A1* | 5/2018 | Gumbo | A61M 5/3291 |
| 2018/0207331 A1 | 7/2018 | Conlan et al. | |
| 2019/0143005 A1 | 5/2019 | Conlan et al. | |

FOREIGN PATENT DOCUMENTS

| | | |
|---|---|---|
| JP | H1050551 | 6/1998 |
| JP | 2010246939 | 11/2010 |
| JP | 2016525897 | 9/2016 |
| WO | 9601085 | 1/1996 |
| WO | 2008028126 | 3/2008 |
| WO | 2012154284 A2 | 11/2012 |
| WO | 20120154284 | 11/2012 |
| WO | 2017030665 | 2/2017 |
| WO | 2018200002 | 11/2018 |

OTHER PUBLICATIONS

Conlan, Bradford, Extended European Search Report for EP Application No. 16837442.9, filed Jul. 1, 2016; dated Jul. 3, 2019, 11 pages.

Conlan, Bradford; Notice of Rejection for Japense Application No. 2018-528192, filed Jul. 1, 2016; dated Aug. 4, 2020; 10 pages.

Conlan, Bradford A.; Partial Supplementary European Search Report for serial No. 16837442.9, filed Jul. 1, 2016, dated Mar. 14, 2019, 12 pgs.

Conlan, Bradford A.; Non-Final Office Action for U.S. Appl. No. 15/199,773, filed Jun. 30, 2016, dated Sep. 27, 2018, 22 pgs.

Conlan, Bradford A.; Issue Notification for U.S. Appl. No. 15/199,773, filed Jun. 30, 2016, dated Jan. 9, 2019, 1 pg.

Conlan, Bradford; Notice of Allowance for U.S. Appl. No. 15/199,773, filed Jun. 30, 2016, dated Nov. 26, 2018, 11 pgs.

Conlan, Bradford A.; Issue Notification for U.S. Appl. No. 15/422,304, filed Feb. 1, 2017, dated Jan. 1, 2019, 1 pg.

Conlan, Bradford A.; Non-Final Office Action for U.S. Appl. No. 15/422,304, filed Feb. 1, 2017, dated Sep. 27, 2018, 16 pgs.

Conlan, Bradford; Corrected Notice of Allowance for U.S. Appl. No. 15/422,304, filed Feb. 1, 2017, dated Dec. 20, 2018, 3 pgs.

Conlan, Bradford; Notice of Allowance for U.S. Appl. No. 15/422,304, filed Feb. 1, 2017, dated Nov. 26, 2018, 12 pgs.

Colan, Bradford A.; International Search Report and Written Opinion for PCT/US17/30247, filed Apr. 28, 2017, dated Jul. 19, 2017, 8 pgs.

Conlan, Bradford A.; International Preliminary Report on Patentability for PCT/US2016/040761, filed Jul. 1, 2016, dated Feb. 20, 2018, 9 pgs.

Conlan, Bradford A.; International Search Report and Written Opinion for PCT/US2016/040761, filed Jul. 1, 2016, dated Sep. 12, 2016, 14 pgs.

Guan, Zhaohui; First Office Action for Chinese Application No. 201680057204.6 filed Jul. 1, 2016; dated Jan. 21, 2020; 8 pages of English translation.

Fornace, Lucas; International Preliminary Report of Patentability for PCT Application No. PCT/US2017/030247, filed Apr. 28, 2017, dated Nov. 7, 2019, 7 pages.

Conlan, Bradford A.; Chinese Office Action for Application No. 2020-509418, filed Apr. 28, 2017, dated Feb. 9, 2021, 9 pgs.

* cited by examiner

MICRO-LIPO NEEDLE DEVICES AND USE THEREOF

CROSS-REFERENCE TO RELATED APPLICATION

This is a continuation-in-part of PCT application No. PCT/US2017/030247, filed Apr. 28, 2017, the teaching of which being incorporated herein in its entirety by reference.

FIELD OF THE INVENTION

The invention relates generally to biomedical sciences and technologies and particularly to tissue harvesting and tissue.

BACKGROUND OF THE INVENTION

The transfer of adipose tissue to various regions of the body is a relatively common cosmetic, therapeutic and structural procedure involving the harvest of adipose tissue from one location and re-implantation of the harvested and, oftentimes processed tissue, in another location (see Coleman 1995; and Coleman 2001). While being largely used for repair of small cosmetic defects such as facial folds, wrinkles, pock marks and divots, transfer of adipose tissue has recently been used for cosmetic and/or therapeutic breast augmentation and reconstruction (Bircoll and Novack 1987; and Dixon 1988), and augmentation of the buttocks (Cardenas-Camarena, Lacouture et al. 1999; de Pedroza 2000; and Peren, Gomez et al. 2000).

In the past, adipose tissue grafts and methods of adipose tissue transfer were plagued with difficulties and side effects including necrosis, absorption of the implant by the body, infection (Castello, Barros et al. 1999; Valdatta, Thione et al. 2001), calcifications and scarring (Huch, Kunzi et al. 1998), inconsistent engraftment, (Eremia and Newman 2000), lack of durability, and other problems arising from lack of neovascularization and necrosis of the transplanted tissue. One of the biggest challenges in adipose tissue transfer is absorption of the implant by the body and volume retention of adipose tissue grafts following transfer. When adipose tissue is harvested or washed, the space between individual pieces of harvested adipose tissue is filled by liquid (e.g., water, blood, tumescent solution, oil). When this tissue/fluid mixture is implanted into a recipient, the liquid portion is rapidly absorbed by the body resulting in loss of volume. The process by which the amount of fluid is removed from the tissue/fluid mixture is frequently referred to as "drying the adipose tissue" or "dehydrating the adipose tissue". The content of red and white blood cells and the like within an adipose tissue graft can also significantly affect the volume of graft retained after graft transplantation, due to induction or exacerbation of an inflammatory response. Another aspect of tissue retention relates to the amount of lipid within the adipose tissue graft. It understood that the presence of free lipid (meaning lipids released from dead or damaged adipocytes; also referred to as oil) in adipose tissue grafts can result in induction or exacerbation of an inflammatory response with substantial phagocytic activity and consequent loss of graft volume.

It is also known that mixing unprocessed adipose tissue with a concentrated population of adipose-derived regenerative cells overcomes many of the problems associated with adipose tissue grafts and adipose tissue transfer, as described above. Specifically, supplementing unprocessed adipose tissue with concentrated populations of adipose-derived cells comprising adipose-derived stem cells increases the weight, vascularization, and retention of fat grafts. (See U.S. Pat. No. 7,390,484 and co-pending U.S. Patent Application Publication No. 2005/0025755, herein expressly incorporated by reference in their entireties). Adipose tissue fragments supplemented, or mixed, with a concentrated population of cells including adipose-derived stem cells exhibit improved neoangiogeneis and perfusion in grafts when compared to unsupplemented grafts of adipose tissue alone in animal models. Further, adipose tissue grafts supplemented with adipose-derived regenerative cells that comprise adipose derived stem cells show increased graft retention and weight over time, when compared to unsupplemented grafts. (See U.S. Patent Application Publication No. 2005/0025755). Further, the processing of adipose tissue in a closed, sterile fluid pathway greatly reduces the chance of infection. The improvement in autologous transfer of adipose tissue seen in the animal models described above has also been replicated in human clinical studies. Nevertheless, the isolation and purification of concentrated populations of adipose-derived regenerative cells comprising adipose-derived stem cells (ADSCs), usually involves a series of washing, digestion, filtration and/or centrifugation steps, which can reduce the yield of viable cells, require mechanical equipment and specialized clinicians, and/or can compromise the quality, appearance, longevity, hydration or efficacy of the graft.

Additionally, stresses could cause undesirable reactions to harvested adipose tissues. Such stresses include, for example, exposure to environmental pathogens, which are mentioned above, and prolonged post-harvest storage, etc.

While devices and systems, for example the devices described in U.S. Pat. No. 9,133,431 B2, were developed to address the above issues and needs, the need for additional approaches to prepare and optimize adipose tissue grafts and implants and to isolate and/or concentrate adipose-derived regenerative cells remains. The embodiments described below address such the above-identified needs.

SUMMARY OF THE INVENTION

In one aspect of the present invention, it is provided a micro-lipo needle device, which device comprising:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention device, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention device, optionally in combination with any of the various embodiments disclosed herein, the needle and cannula are adapted to form a matched set forming a concentric seal, limiting leakage.

In some embodiments of the invention device, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention device, optionally in combination with any of the various embodiments disclosed herein, the mechanism comprises a track that allows the needle to slide on in 1 dimension.

In some embodiments of the invention device, optionally in combination with any of the various embodiments disclosed herein, the mechanism comprises a spring mechanism to ensure the needle is returned to a safe position after use.

In some embodiments of the invention device, optionally in combination with any of the various embodiments disclosed herein, the membrane is a silicone membrane.

In some embodiments of the invention device, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention device, optionally in combination with any of the various embodiments disclosed herein, the assembly further comprises a sweep mechanism configured to allow the cannula to sweep over a range of certain degrees.

In some embodiments of the invention device, optionally in combination with any of the various embodiments disclosed herein, the sweep mechanism comprises vertical positions to allow harvesting tissue in multiple planes.

In some embodiments of the invention device, optionally in combination with any of the various embodiments disclosed herein, the sweep mechanism comprises detents every 10 degrees and allows the cannula to sweep over a range of 40 degrees.

In some embodiments of the invention device, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention device, optionally in combination with any of the various embodiments disclosed herein, the device is a one-time-use and disposable ("single patient, single use aka SPSU") device.

In some embodiments of the invention device, optionally in combination with any of the various embodiments disclosed herein, the main housing comprises a linear, flat skin contact side or a curved skin contact side.

In some embodiments of the invention device, optionally in combination with any of the various embodiments disclosed herein, the cannua is attached to a tissue filtration/purification system.

In some embodiments of the invention device, optionally in combination with any of the various embodiments disclosed herein, the tissue filtration/purification system is a Puregraft™ bag or Puregraft™ syringe.

In a second aspect of the present invention, it is provided a method of micro-liposuction, comprising:

harvesting a volume of fat tissue from a subject using a micro-lipo needle device of invention.

In some embodiments of the invention method, optionally in combination with any of the various embodiments disclosed herein, the device comprises:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention method, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention method, optionally in combination with any of the various embodiments disclosed herein, the needle and cannula are adapted to form a matched set forming a concentric seal, limiting leakage.

In some embodiments of the invention method, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention method, optionally in combination with any of the various embodiments disclosed herein, the mechanism comprises a track that allows the needle to slide on in 1 dimension.

In some embodiments of the invention method, optionally in combination with any of the various embodiments disclosed herein, the mechanism comprises a spring mechanism to ensure the needle is returned to a safe position after use.

In some embodiments of the invention method, optionally in combination with any of the various embodiments disclosed herein, the membrane is a silicone membrane.

In some embodiments of the invention method, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention method, optionally in combination with any of the various embodiments disclosed herein, the assembly further comprises a sweep mechanism configured to allow the cannula to sweep over a range of certain degrees.

In some embodiments of the invention method, optionally in combination with any of the various embodiments disclosed herein, the sweep mechanism comprises vertical positions to allow harvesting tissue in multiple planes.

In some embodiments of the invention method, optionally in combination with any of the various embodiments disclosed herein, the sweep mechanism comprises detents every 10 degrees and allows the cannula to sweep over a range of 40 degrees.

In some embodiments of the invention method, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention method, optionally in combination with any of the various embodiments disclosed herein, the main housing comprises a linear, flat skin contact side or a curved skin contact side.

In some embodiments of the invention method, optionally in combination with any of the various embodiments disclosed herein, the device is a one-time-use and disposable SPSU device.

In some embodiments of the invention method, optionally in combination with any of the various embodiments disclosed herein, the cannua is attached to a tissue filtration/purification system.

In some embodiments of the invention method, optionally in combination with any of the various embodiments disclosed herein, the tissue filtration/purification system is a Puregraft™ bag or Puregraft™ syringe.

In some embodiments of the invention method, optionally in combination with any of the various embodiments disclosed herein, the subject is a human being.

In a further aspect of the present invention, it is provided a method of fabricating a micro-lipo needle device, comprising:

providing a design of the micro-lipo needle device;

providing materials and parts to effect the design of the micro-lipo needle device; and forming the micro-lipo needle device.

In some embodiments of the invention method, optionally in combination with any of the various embodiments disclosed herein, the device comprises:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention method, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention method, optionally in combination with any of the various embodiments disclosed herein, the needle and cannula are adapted to form a matched set forming a concentric seal, limiting leakage.

In some embodiments of the invention method, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention method, optionally in combination with any of the various embodiments disclosed herein, the mechanism comprises a track that allows the needle to slide on in 1 dimension.

In some embodiments of the invention method, optionally in combination with any of the various embodiments disclosed herein, the mechanism comprises a spring mechanism to ensure the needle is returned to a safe position after use.

In some embodiments of the invention method, optionally in combination with any of the various embodiments disclosed herein, the membrane is a silicone membrane.

In some embodiments of the invention method, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention method, optionally in combination with any of the various embodiments disclosed herein, the assembly further comprises a sweep mechanism configured to allow the cannula to sweep over a range of certain degrees.

In some embodiments of the invention method, optionally in combination with any of the various embodiments disclosed herein, the sweep mechanism comprises vertical positions to allow harvesting tissue in multiple planes.

In some embodiments of the invention method, optionally in combination with any of the various embodiments disclosed herein, the sweep mechanism comprises detents every 10 degrees and allows the cannula to sweep over a range of 40 degrees.

In some embodiments of the invention method, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention method, optionally in combination with any of the various embodiments disclosed herein, the main housing comprises a linear, flat skin contact side or a curved skin contact side.

In some embodiments of the invention method, optionally in combination with any of the various embodiments disclosed herein, the device is a one-time-use and disposable SPSU device.

In some embodiments of the invention method, optionally in combination with any of the various embodiments disclosed herein, the cannua is attached to a tissue filtration/purification system.

In some embodiments of the invention method, optionally in combination with any of the various embodiments disclosed herein, the tissue filtration/purification system is a Puregraft™ bag or Puregraft™ syringe.

DETAILED DESCRIPTION OF EMBODIMENTS OF THE INVENTION

Definitions

Figure 1A:
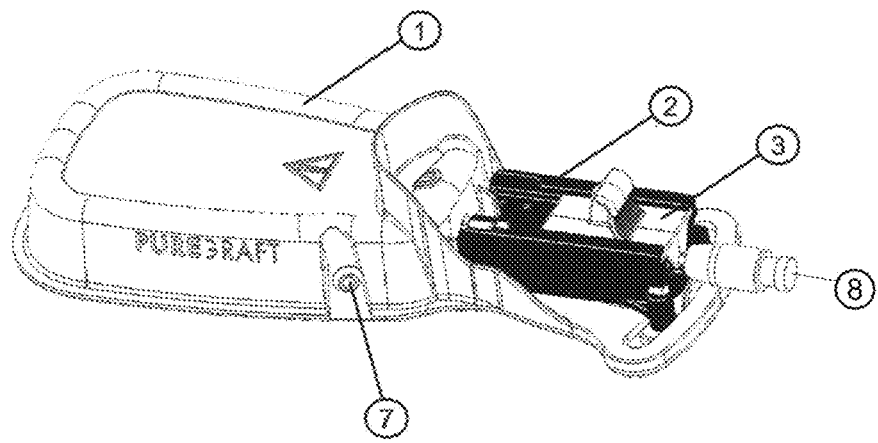
FIG. 1A shows a micro-lipo device having a main housing, a needle carriage housing, a needle carriage, and a vacuum port.

As used herein, the term "adipose tissue" is used interchangeably with the term "fat", the meaning of which is well known to a person of ordinary skill in the art.

As used herein, the term "adipose tissue removal" or "tissue removal" or "harvesting" or "liposuction" are used interchangeably to mean remove an amount of adipose tissue from a live subject such as a male or female patient.

As used herein, the term "tissue filtration/purification system" refers to a device or system used to purify harvested fat tissue or filter off undesirable component(s) from harvested fat tissue. Examples of such a tissue filtration/purification system is a Puregraft™ system or bag as described in U.S. Pat. No. 9,133,431 or a Puregraft™ syringe as described in U.S. patent application Ser. No. 15/422,304, filed on Feb. 1, 2017 and U.S. patent application Ser. No. 15/199,773, filed on Jun. 30, 2016. The teachings in the patent and patent applications identified herein are incorporated in their entirety by reference.

Whenever is used, the term "collapsible" refers to the attribute of a material capable of collapsing under pressure or vacuum or capable of changing of shape or contour or of deformation in response to pressure change, and as such, in some embodiments, the term "collapsible" can mean deformable. An example of a material that is collapsible is a plastic or polymeric material forming a bag, e.g., a bag that is described in U.S. patent application Ser. No. 12/771,985, the teachings of which is incorporated herein by reference in its entirety.

Micro-Lipo Needle Device

In one aspect of the present invention, it is provided a micro-lipo needle device, which device comprising:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention device, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention device, optionally in combination with any of the various embodiments disclosed herein, the needle and cannula are adapted to form a matched set forming a concentric seal, limiting leakage.

In some embodiments of the invention device, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention device, optionally in combination with any of the various embodiments disclosed herein, the mechanism comprises a track that allows the needle to slide on in 1 dimension.

In some embodiments of the invention device, optionally in combination with any of the various embodiments disclosed herein, the mechanism comprises a spring mechanism to ensure the needle is returned to a safe position after use.

In some embodiments of the invention device, optionally in combination with any of the various embodiments disclosed herein, the membrane is a silicone membrane.

In some embodiments of the invention device, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention device, optionally in combination with any of the various embodiments disclosed herein, the assembly further comprises a sweep mechanism configured to allow the cannula to sweep over a range of certain degrees.

In some embodiments of the invention device, optionally in combination with any of the various embodiments disclosed herein, the sweep mechanism comprises vertical positions to allow harvesting tissue in multiple planes.

In some embodiments of the invention device, optionally in combination with any of the various embodiments disclosed herein, the sweep mechanism comprises detents every 10 degrees and allows the cannula to sweep over a range of 40 degrees.

In some embodiments of the invention device, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention device, optionally in combination with any of the various embodiments disclosed herein, the main housing comprises a linear, flat skin contact side or a curved skin contact side.

In some embodiments of the invention device, optionally in combination with any of the various embodiments disclosed herein, the device is a one-time-use and disposable SPSU device.

In some embodiments of the invention device, optionally in combination with any of the various embodiments disclosed herein, the cannua is attached to a tissue filtration/purification system.

In some embodiments of the invention device, optionally in combination with any of the various embodiments disclosed herein, the tissue filtration/purification system is a Puregraft™ bag or Puregraft™ syringe.

In one aspect of the present invention, it is provided a micro-lipo needle device. Such device includes needles and cannula for fat harvest, which can be used independently or together with a liposuction fat transfer system such as a syringe filtration system as described in U.S. patent application Ser. No. 15/422,304, entitled "Liposuction Device and Use thereof".

In some embodiments, an invention device includes one or more of the following elements:

a large cavity that is designed to lift, via vacuum, the skin and fat to be liposuctioned. This cavity limits the area of the body that can be liposuctioned, making it safer and less reliant on doctor skill and knowhow. As used herein, the term "large cavity" refers to a dimension that is sufficient to allow a desired volume of skin and fat to be lifted and liposuctioned, and the dimension defines and limits the area of the body to be liposuctioned such that the liposuction will not go beyond the area and the lifted volume of fat, providing a safe-guard to allow the liposuction to be formed with an enhanced safety assurance (see also FIGS. 1A and 1B). In some embodiments, the invention device can include a safety valve which allows one to limits the vacuum to a certain degree (e.g., 15 in Hg) to limit skin trauma. The valve can be located in the vacuum tubing, but could also be part of the unit;

a needle to puncture the skin that has been lifted to fill up the cavity. In some embodiments, the needle can be designed to be part of a mechanism that limits its travel for safety. For example, it can be on a track and can only slide in 1 dimension. In some embodiments, the mechanism has a spring to ensure the needle is returned to the safe position after use. The travel of the needle is designed so it can only poke through the dermis, just enough to allow a cannula to penetrate the dermis;

a cannula to be inserted through the inner portion of the needle (concentric). The cannula is then also constrained to 1 dimension (fore and aft), whose travel is limited such that no harm can be done to the patient. The cannula can only traverse a limited portion of the body, which is constrained in the cavity. The needle and cannula are adapted to form a matched set forming a concentric seal, limiting leakage. In some embodiments, while the cannula can only be allowed to move though the needle, the entire needle/cannula assembly can articulate to allow the cannula to cover more of the body volume to be liposuction (also FIGS. 2A and 2B). For example, the device can have a mechanism that allows the cannula to sweep over a range of 40 degrees (for example, with detents every 10 degrees) and has two vertical positions for harvesting tissue in multiple planes. For example, the device can be made to have one position at 10 mm below the skin and another at 6 mm below the skin. This allows for safe harvesting of tissue without the risk of going too deep. In summary, the needle/cannula can slide in 1 dimension, but the assembly can navigate the body in 3 dimensions;

an optional vacuum interlock. Optionally, the device can include a vacuum interlock feature (FIG. 7) that prevents the needle from entering the cavity unless the cavity is under sufficient vacuum (which practically guarantees that the skin has been safely raised into position). This interlock will prevent someone from trying to puncture the skin before it has been lifted into the cavity, or will prevent a needle prick to an operator or clean-up crew. In some embodiments, a spring (e.g., a stainless compressing spring) can be loaded to the needle, which is sufficient to keep the needle out of harm's way; and/or a silicone membrane that seals the needle entry window to prevent leakage.

Figure 7:
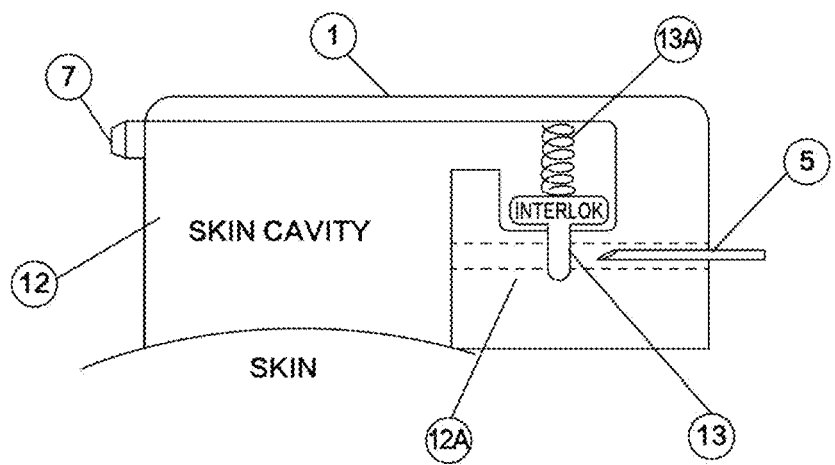
FIG. 7 shows an embodiment of a vacuum interlock element in some embodiments of the invention device.

Referring to FIG. 7, a vacuum interlock 13 is provided inside the cavity formed by the main housing 1 and skin of user, the vacuum interlock 13 being mounted on a site of ceiling of the main housing with a spring element 13a. When the vacuum inside the cavity 12a generated via vacuum port 7 is insufficient, a volume of the adipose tissue lifted up into the cavity, 12, would be insufficient such that the spring element 13a would stay in an extended state to block the entrance of a needle. Conversely, when the vacuum inside the cavity generated via vacuum port 7 is sufficient, a volume of the adipose tissue lifted up into the cavity, 12, would be sufficient such that the spring element 13a would be pushed-down by the adipose tissue to make room for entrance of the needle 5.

In some embodiments, all of the above is one-time-use and disposable (single patient, single use aka SPSU), which would avoid cross-contamination among the patients.

Some further embodiments of the invention device are described in FIGS. 1-2: FIG. 1A shows a prototype of a micro-lipo needle device having a main housing 1, carriage housing 2, needle carriage 3, and a vacuum port 7.

Figure 1B:
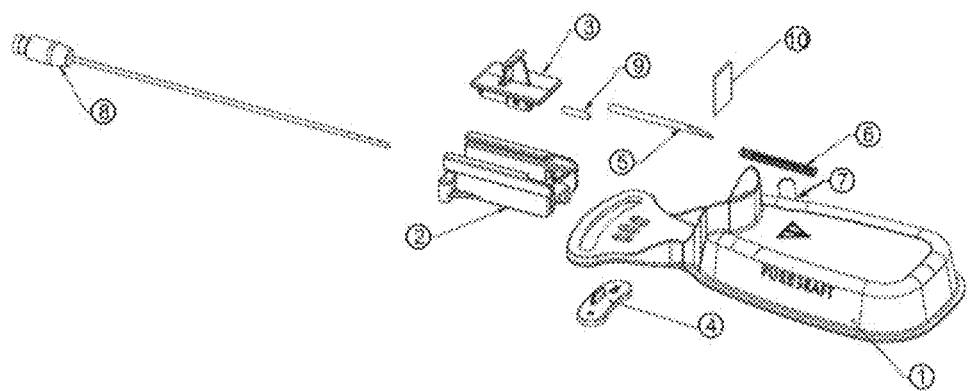
FIG. 1B shows the micro-lipo device of FIG. 1A in more detail.

FIG. 1B shows the micro-lipo needle device of FIG. 1A in more detail. Referring to FIG. 1B, the micro-lipo needle device includes the following elements: a main housing 1, a needle carriage housing 2, a needle carriage 3, a needle carriage washer 4, a lancet point needle 5, a compressing spring 6, a vacuum port 7, a cannula 8, a needle bonding adhesive 9, and a silicone sealing membrane 10.

Figure 2A:
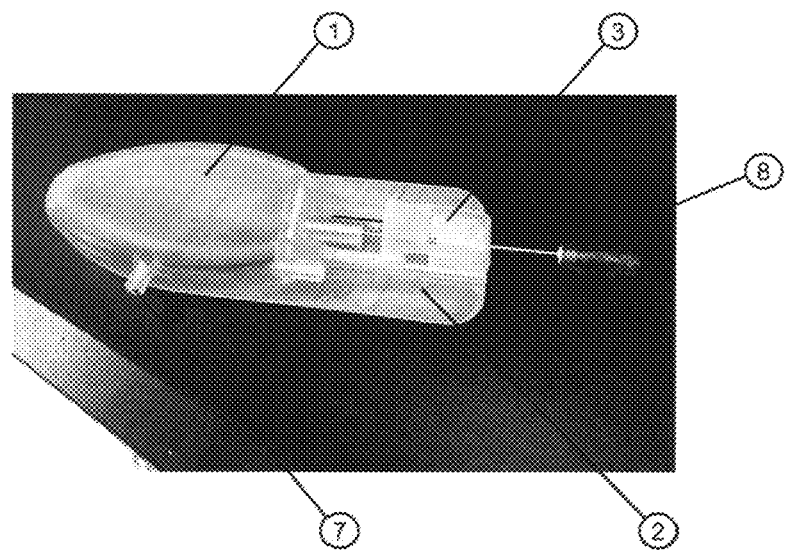
FIG. 2A shows a 3D printed version of invention device shown with cannula (blue/silver) inserted from right side.
Figure 2B:
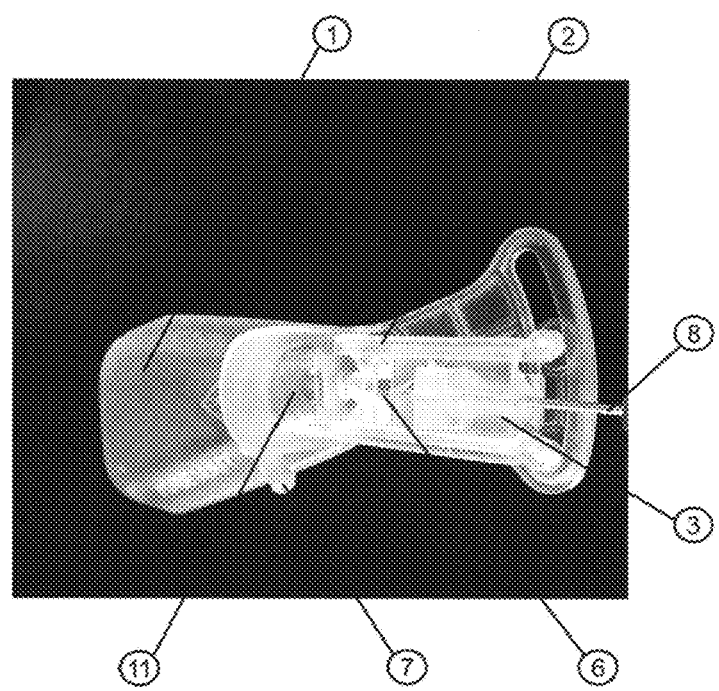
FIG. 2B shows an embodiment of invention device showing articulation of needle/cannula. Shown is the left-most position.

FIG. 2A shows an embodiment of micro-lipo needle device shown with cannula (blue/silver) inserted from right side. FIG. 2B is the micro-lipo needle device of FIG. 2A showing articulation, 11, of needle/cannula.

Method of Use

In a second aspect of the present invention, it is provided a method of performing micro-liposuction, comprising:

harvesting a volume of fat tissue from a subject using a micro-lipo needle device of invention.

In some embodiments of the invention method, optionally in combination with any of the various embodiments disclosed herein, the device comprises:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention method, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention method, optionally in combination with any of the various embodiments disclosed herein, the needle and cannula are adapted to form a matched set forming a concentric seal, limiting leakage.

In some embodiments of the invention method, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention method, optionally in combination with any of the various embodiments disclosed herein, the mechanism comprises a track that allows the needle to slide on in 1 dimension.

In some embodiments of the invention method, optionally in combination with any of the various embodiments disclosed herein, the mechanism comprises a spring mechanism to ensure the needle is returned to a safe position after use.

In some embodiments of the invention method, optionally in combination with any of the various embodiments disclosed herein, the membrane is a silicone membrane.

In some embodiments of the invention method, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention method, optionally in combination with any of the various embodiments disclosed herein, the assembly further comprises a sweep mechanism configured to allow the cannula to sweep over a range of certain degrees.

In some embodiments of the invention method, optionally in combination with any of the various embodiments disclosed herein, the sweep mechanism comprises vertical positions to allow harvesting tissue in multiple planes.

In some embodiments of the invention method, optionally in combination with any of the various embodiments disclosed herein, the sweep mechanism comprises detents every 10 degrees and allows the cannula to sweep over a range of 40 degrees.

In some embodiments of the invention method, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention method, optionally in combination with any of the various embodiments disclosed herein, the main housing comprises a linear, flat skin contact side or a curved skin contact side.

In some embodiments of the invention method, optionally in combination with any of the various embodiments disclosed herein, the device is a one-time-use and disposable SPSU device.

In some embodiments of the invention method, optionally in combination with any of the various embodiments disclosed herein, the cannua is attached to a tissue filtration/purification system.

In some embodiments of the invention method, optionally in combination with any of the various embodiments disclosed herein, the tissue filtration/purification system is a Puregraft™ bag or Puregraft™ syringe.

In some embodiments of the invention method, optionally in combination with any of the various embodiments disclosed herein, the subject is a human being.

The device of invention can use to remove or harvest adipose tissue from an area of the body. Exemplary procedures of using the device are provided below:

1) Prepare patient for liposuction;
2) Introduce local anesthesia, if needed;
3) Open sterile micro-lipo device of invention. Place on patient skin in prepared area and (using supplied syringe and tubing) pump vacuum until resistance is felt and skin is visibly in the cavity (optionally, connect to vacuum system set to 15 in Hg).
4) Attach included harvest syringe (or PG syringe) to the harvest cannula and set aside.
5) Using one hand, drive the needle mechanism into the skin to puncture (if needle will not move forward, check vacuum of step 3). While the needle is being held in the inserted position, quickly introduce the cannula through the needle and into the patient. Release the needle to allow it to exit the patient and return to the sheathed position.
6) Create vacuum in syringe by pulling it open and locking it in the open position.
7) Liposuction patient by gently pulling cannula/syringe back and forth until syringe is full of lipoaspirate. If necessary, harvest from another location to fill syringe.
8) Remove cannula from patient, release vacuum, and remove micro-lipo device from patient and discard.
9) Apply bandage to needle entry site.
10) If using a Puregraft syringe for filtration, follow instructions to prepare fat for transfer.

Figure 3:
FIG. 3 shows a 3D printed and sterile version of micro-lipo needle device being successfully used on a human subject.

FIG. 3 shows that fat tissue harvesting is successfully performed using a micro-lipo needle device of invention The micro-lipo device of invention contains a needle for piercing and gaining access to human fat tissue in a safe and controlled fashion. The device of invention can be made to have various shapes designed for removing small amount of fat tissue from certain specific areas of the body: for example, under the chin (to reduce "double chin"—see FIGS. 5A-5E of the curved device), in the abdomen area (to help create "six pack" definition—see FIGS. 4A-4F of "linear" device), love handles, pubic area, etc.

The use includes biomedical and cosmetic applications on a subject. Cosmetic applications can be, for example, organ reshaping or augmentation. Biomedical applications can be, for example, tissue grafting, and cell therapy or tissue regenerative therapies.

Method of Fabrication

In a further aspect of the present invention, it is provided a method of fabricating a micro-lipo needle device, comprising:

providing a design of the micro-lipo needle device;

providing materials and parts to effect the design of the micro-lipo needle device; and forming the micro-lipo needle device.

In some embodiments of the invention method, optionally in combination with any of the various embodiments disclosed herein, the device comprises:

a main housing configured to provide a cavity, which cavity being configured to be communicateble with a vacuum source such that when the main housing is placed on an area of a body the vacuum source generates a degree of vacuum to cause a volume of skin and fat to be lifted so as to fill up the cavity;

a needle to puncture the skin that has been lifted to fill up the cavity;

a cannula to be inserted through the inner portion of the needle wherein the cannula is concentric with the needle and constrained to 1 dimension, the travel of which being limited such that no harm is done to a patient receiving the cannula;

a membrane that is configured to seal an entry window of the needle to prevent leakage; and an optional assembly comprising the needle and the cannula.

In some embodiments of the invention method, optionally in combination with any of the various embodiments disclosed herein, the device further comprises a vacuum interlock element that prevents the needle from entering the cavity unless the cavity is under sufficient vacuum to ensure the skin being raised into a safe position for liposuction.

In some embodiments of the invention method, optionally in combination with any of the various embodiments disclosed herein, the needle and cannula are adapted to form a matched set forming a concentric seal, limiting leakage.

In some embodiments of the invention method, optionally in combination with any of the various embodiments disclosed herein, the device further comprises a mechanism that is configured to safe-guard travel of the needle such that the travel of needle only pokes through the dermis without further insertion into the fat tissue to allow a cannula to penetrate the dermis.

In some embodiments of the invention method, optionally in combination with any of the various embodiments disclosed herein, the mechanism comprises a track that allows the needle to slide on in 1 dimension.

In some embodiments of the invention method, optionally in combination with any of the various embodiments disclosed herein, the mechanism comprises a spring mechanism to ensure the needle is returned to a safe position after use.

In some embodiments of the invention method, optionally in combination with any of the various embodiments disclosed herein, the membrane is a silicone membrane.

In some embodiments of the invention method, optionally in combination with any of the various embodiments disclosed herein, the device comprises the assembly, which assembly comprising a needle carriage housing and a needle carriage, which articulate to allow the cannula to cover a larger volume of fat tissue for liposuction, wherein the assembly is configured to be able to navigate the body in 3 dimensions.

In some embodiments of the invention method, optionally in combination with any of the various embodiments disclosed herein, the assembly further comprises a sweep mechanism configured to allow the cannula to sweep over a range of certain degrees.

In some embodiments of the invention method, optionally in combination with any of the various embodiments disclosed herein, the sweep mechanism comprises vertical positions to allow harvesting tissue in multiple planes.

In some embodiments of the invention method, optionally in combination with any of the various embodiments disclosed herein, the sweep mechanism comprises detents every 10 degrees and allows the cannula to sweep over a range of 40 degrees.

In some embodiments of the invention method, optionally in combination with any of the various embodiments disclosed herein, the sweep mechanism comprises 2 or more vertical positions at anywhere from 2-20 mm below the skin to allow harvesting tissue in two planes defined by the 2 or more vertical positions.

In some embodiments of the invention method, optionally in combination with any of the various embodiments disclosed herein, the main housing comprises a linear, flat skin contact side or a curved skin contact side.

In some embodiments of the invention method, optionally in combination with any of the various embodiments disclosed herein, the device is a one-time-use and disposable SPSU device.

In some embodiments of the invention method, optionally in combination with any of the various embodiments disclosed herein, the cannua is attached to a tissue filtration/purification system.

In some embodiments of the invention method, optionally in combination with any of the various embodiments disclosed herein, the tissue filtration/purification system is a Puregraft™ bag or Puregraft™ syringe.

EXAMPLES

Example 1

Designs of exemplary micro-lipo needle devices of invention are shown in FIGS. 1A, 1B, 2A, and 2B.

Example 2

An embodiment of invention is made by 3D printing, which is shown by FIGS. 2A-2B.

Example 3

An embodiment of the invention micro-lipo needle device is used for liposuction in a human subject following the procedures of invention described above. FIG. 3 shows that liposuction using the micro-lipo needle device is successful.

Example 4

Figure 4A:
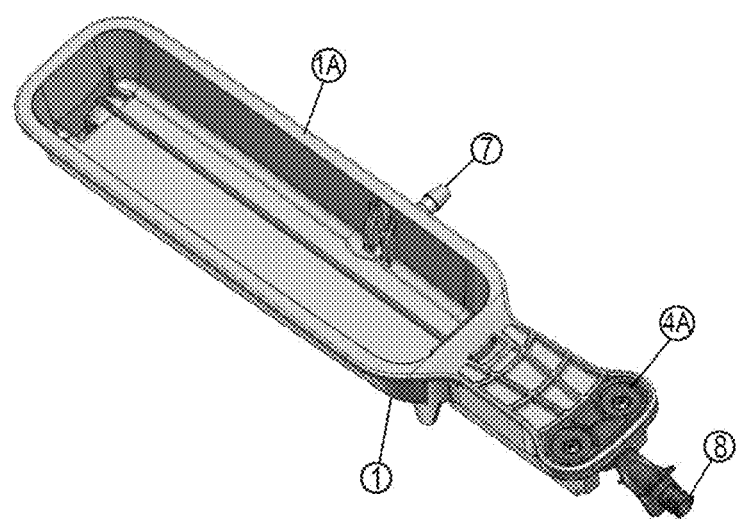
FIGS. 4A-4F show an embodiment of the invention device having a linear, flat skin contact side.
Figure 4B:
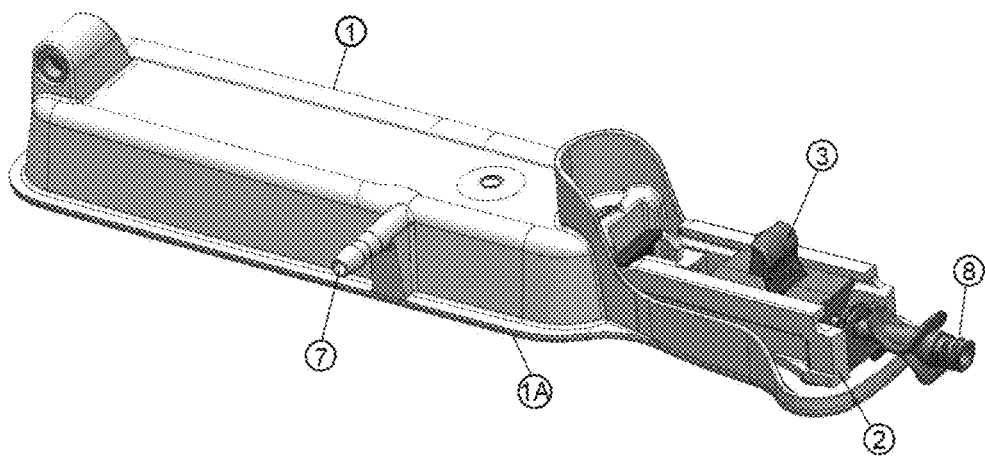
Figure 4C:
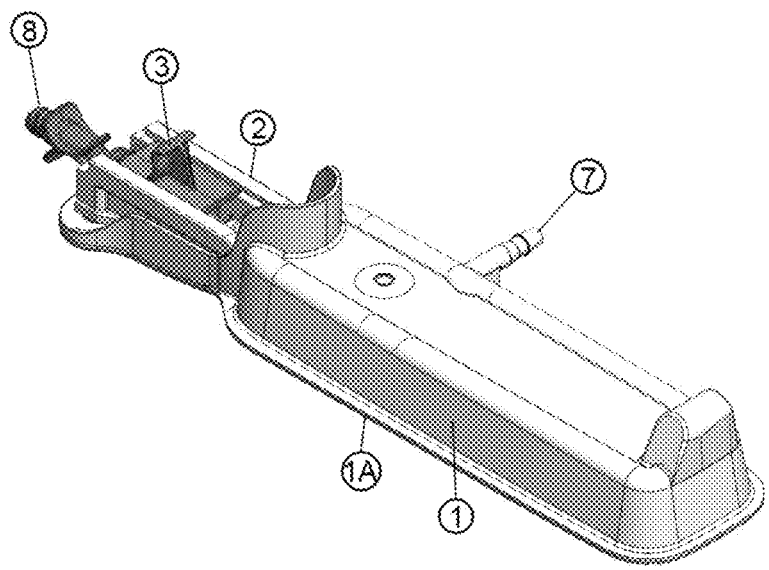
Figure 4D:
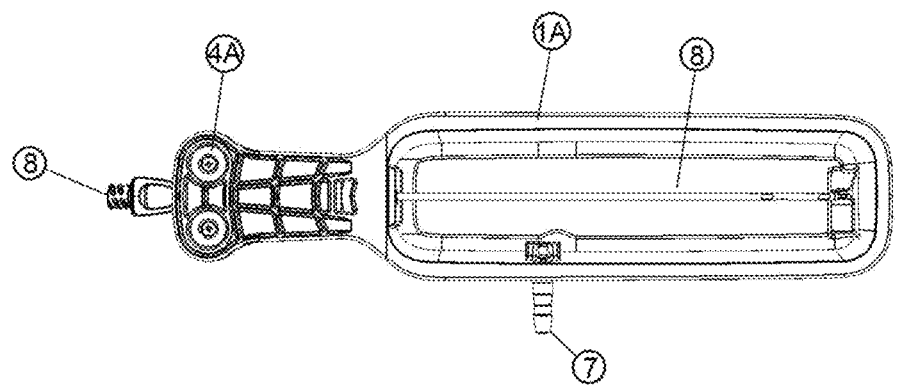
Figure 4E:
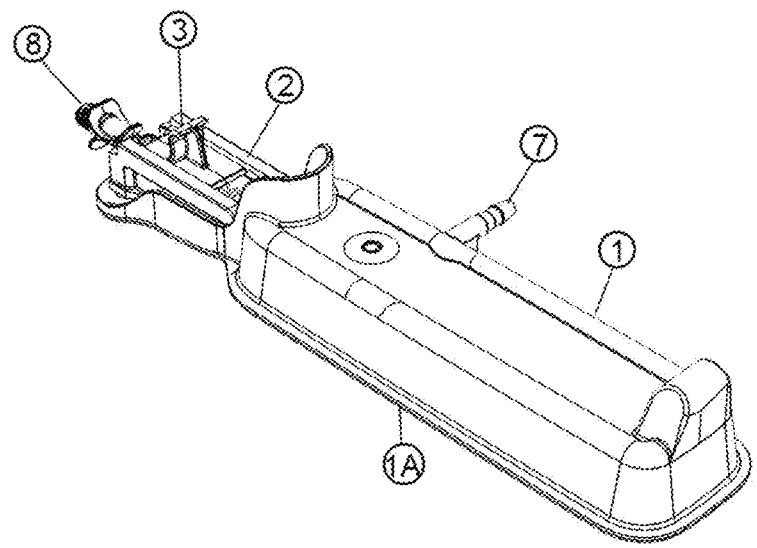
Figure 4F:
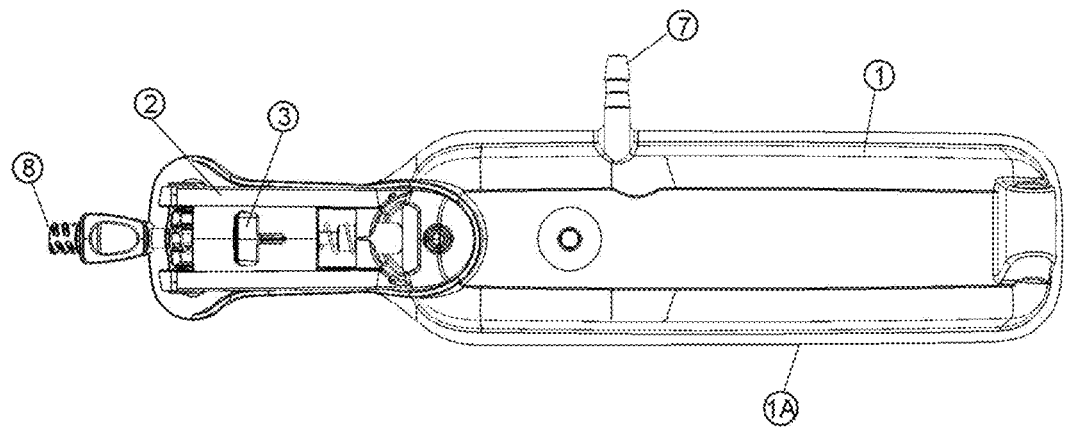

FIGS. 4A-4F show an embodiment of the invention device. FIG. 4A shows an upside down/flip view of an embodiment of invention device, showing a main housing 1 having a linear, flat skin contact side 1A, a needle carriage housing 2, a needle carriage washer 4 showing a skin facing side 4A, a vacuum port 7, and a cannula 8. FIG. 4D shows a line-drawing depiction of the upside down/flip view of the embodiment of invention device, showing a main housing 1 having a linear, flat skin contact side 1A, a needle carriage housing 2, a needle carriage washer 4 showing a skin facing side 4A, a vacuum port 7, and a cannula 8. FIGS. 4B, 4C and 4E each show a top-down side view of the embodiment of invention device, showing a main housing 1 having a linear/flat skin contact side 1A, a needle carriage housing 2, a needle carriage 3, a vacuum port 7, and a cannula 8. FIG. 4F shows a line-drawing depiction of a top-down side view of the embodiment of invention device, showing a main housing 1 having a linear, flat skin contact side 1A, a needle carriage housing 2, a needle carriage 3, a vacuum port 7, and a cannula 8.

Example 5

Figure 5A:
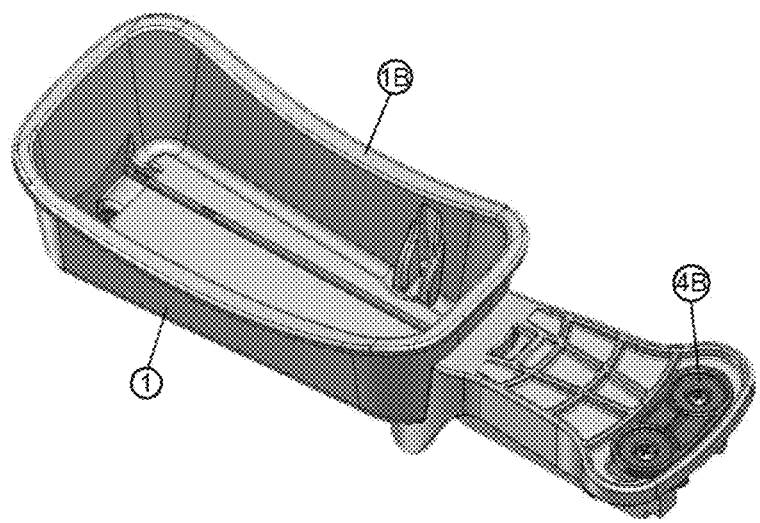
FIGS. 5A-5E show an embodiment of the invention device having a curved skin contact side.
Figure 5B:
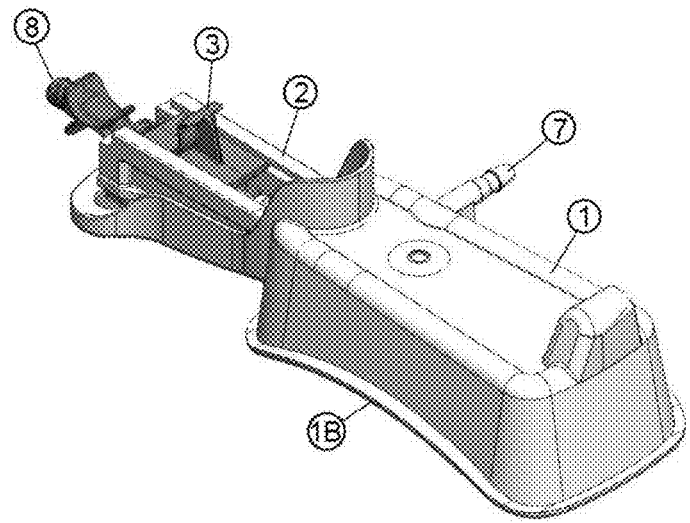
Figure 5C:
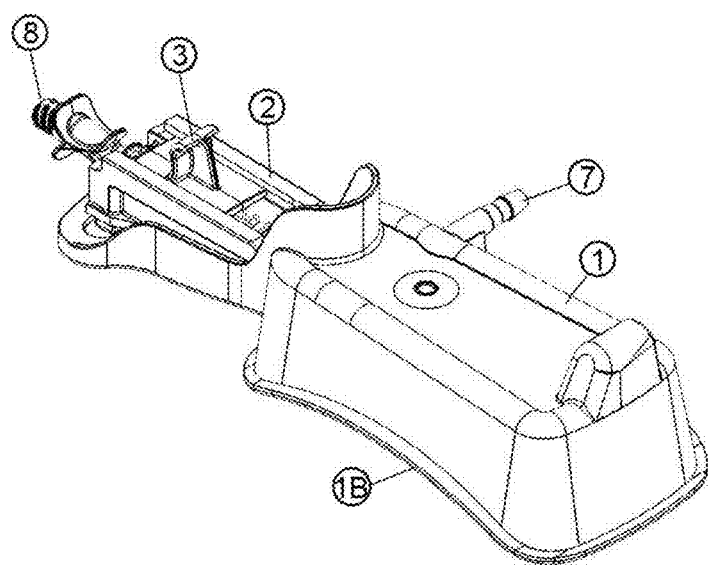
Figure 5D:
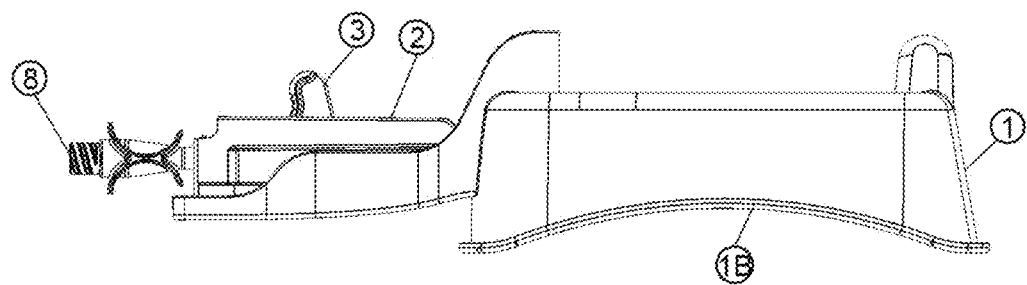
Figure 5E:
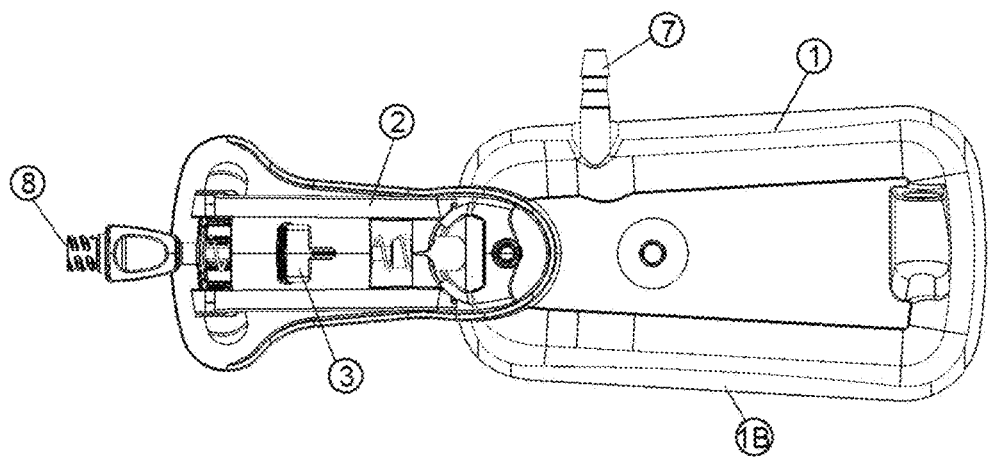

FIGS. 5A-5E show an embodiment of the invention device. FIG. 5A shows an upside down/flip view of an embodiment of invention device, showing a main housing 1 having a curved skin contact side 1B, a needle carriage washer 4 showing a skin facing side 4A, and a vacuum port 7. FIGS. 5B and 5C each show a top-down side view of the embodiment of invention device, showing a main housing 1 having a curved skin contact side 1B, a needle carriage housing 2, a needle carriage 3, a vacuum port 7, and a cannula 8. FIG. 5D shows a line-drawing depiction of a top-down side view of the embodiment of invention device, showing a main housing 1 having a curved skin contact side 1B, a needle carriage housing 2, a needle carriage 3, and a cannula 8. FIG. 5E shows a line-drawing depiction of a top-down view of the embodiment of invention device, showing a main housing 1 having a curved skin contact side 1B, a needle carriage housing 2, a needle carriage 3, a vacuum port 7, and a cannula 8.

Example 6

Figure 6:
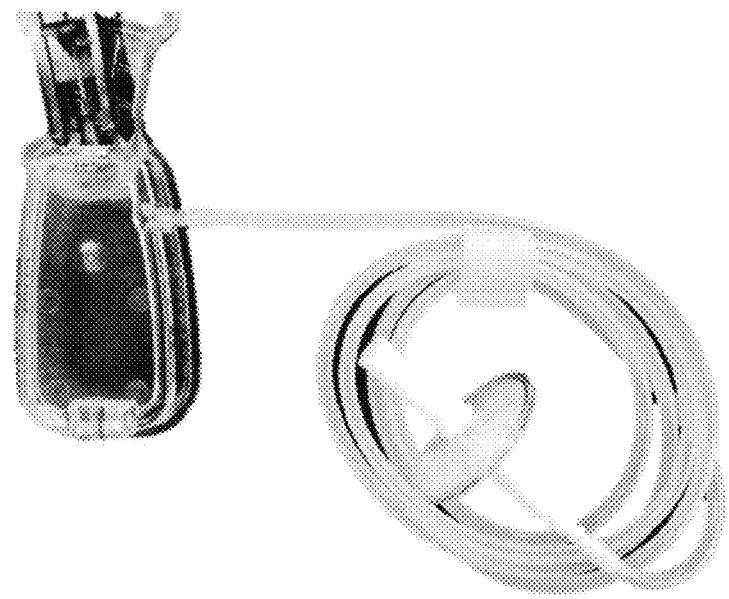
FIG. 6 shows an embodiment of invention device made and ready for use.

FIG. 6 shows an embodiment of invention device made and ready for use, its vacuum port being connected to a flexible tubing.

While various embodiments of the present invention have been described and shown herein, it will be obvious that such embodiments are provided by way of example only. Numerous variations, changes and substitutions may be made without departing from the invention herein. Accordingly, it is intended that the invention be limited only by the spirit and scope of the appended claims.

The teachings of the references, including patents and patent related documents, cited herein are incorporated herein in their entirety to the extent not inconsistent with the teachings herein.

We claim:

1. A micro-lipo needle device, comprising:
    a main housing configured to provide a cavity, wherein the cavity is configured to communicate with a vacuum source that generates a degree of vacuum to cause a volume of skin and fat to be lifted into the cavity;
    a hypodermic needle comprising a point and a butt and defining a passage between the point and the butt;
    a carriage housing affixed to the main housing and comprising a portion defining a track along a longitudinal axis;
    a needle carriage comprising a portion inserted into the portion defining the track and a portion having a surface perpendicular to the longitudinal axis of the carriage housing, the portion having the perpendicular surface affixed to the butt of the hypodermic needle, and the affixed hypodermic needle having a longitudinal axis parallel with the longitudinal axis of the carriage housing;
    a spring affixed to the perpendicular surface of the needle carriage and an inner surface of the carriage housing proximate the cavity and surrounding the hypodermic affixed to the perpendicular surface of the needle carriage;
    a cannula to be inserted through the passage between the point and the butt of the hypodermic needle, the cannula having a diameter smaller than a diameter of the passage.

2. The micro-lipo needle device according to claim 1, further comprises a vacuum interlock element that prevents the hypodermic needle from entering the cavity unless the cavity is under sufficient vacuum.

3. The micro-lipo needle device according to claim 1, wherein the hypodermic needle and the cannula are adapted to form a concentric seal between an outer surface of the cannula and an inner surface of the passage.

4. The micro-lipo needle device according to claim 1, further comprising a silicone membrane configured to seal an entry window of the needle to prevent leakage.

5. The micro-lipo needle device according to claim 1, the carriage housing further comprises a sweep mechanism configured to limit angular movement of the cannula.

6. The micro-lipo needle device according to claim 5, wherein the sweep mechanism comprises vertical positions to allow harvesting tissue in multiple planes.

7. The micro-lipo needle device according to claim 6, wherein the sweep mechanism comprises 2 or more vertical positions at anywhere from 2-20 mm below the skin to allow harvesting tissue in two planes defined by the 2 or more vertical positions.

8. The micro-lipo needle device according to claim 5, wherein the sweep mechanism comprises detents every 10 degrees and allows the cannula to sweep over a range of 40 degrees.

9. The micro-lipo needle device according to claim 1, which is a one-time-use and disposable device.

10. The micro-lipo needle device according to claim 1, wherein the main housing comprises a linear, flat skin contact side or a curved skin contact side.

11. The micro-lipo needle device according to claim 1, wherein the cannula is attached to a tissue filtration/purification system.

12. A method of performing micro-liposuction on a subject, comprising applying a micro-lipo needle device to the subject, and harvesting a volume of fat tissue from the subject, the micro-lipo needle device comprising:
    a main housing configured to provide a cavity, wherein the cavity is configured to communicate with a vacuum source that generates a degree of vacuum to cause a volume of skin and fat to be lifted into the cavity;
    a hypodermic needle comprising a point and a butt and defining a passage between the point and the butt;
    a carriage housing affixed to the main housing and comprising a portion defining a track along a longitudinal axis;
    a needle carriage comprising a portion inserted into the portion defining the track and a portion having a surface perpendicular to the longitudinal axis of the carriage housing, the portion having the perpendicular surface affixed to the butt of the hypodermic needle, and the affixed hypodermic needle having a longitudinal axis parallel with the longitudinal axis of the carriage housing;
    a spring affixed to the surface of the needle carriage and an inner surface of the carriage housing proximate the cavity and surrounding the hypodermic needle affixed to the surface of the needle carriage;
    a cannula to be inserted through the passage between the point and the butt of the hypodermic needle, the cannula having a diameter smaller than a diameter of the passage.

13. The method according to claim 12, wherein the main housing comprises a linear, flat skin contact side or a curved skin contact side.

14. A method of fabricating a micro-lipo needle device, comprising:
providing a design of the micro-lipo needle device comprising a main housing, a hypodermic needle, a carriage housing, a needle carriage, a spring, and a cannula, forming the micro-lipo needle device, wherein:
the main housing configured to provide a cavity, wherein the cavity is configured to communicate with a vacuum source that generates a degree of vacuum to cause a volume of skin and fat to be lifted into the cavity;
the hypodermic needle comprising a point and a butt and defining a passage between the point and the butt;
the carriage housing affixed to the main housing and comprising a portion defining a track along a longitudinal axis;
the needle carriage comprising a portion inserted into the portion defining the track and a portion having a surface perpendicular to the longitudinal axis of the carriage housing, the portion having the perpendicular surface affixed to the butt of the hypodermic needle, and the affixed hypodermic needle having a longitudinal axis parallel with the longitudinal axis of the carriage housing;
the spring affixed to the surface of the needle carriage and an inner surface of the carriage housing proximate the cavity and surrounding the hypodermic needle affixed to the perpendicular surface of the needle carriage;
the cannula to be inserted through the passage between the point and the butt of the hypodermic needle, the cannula having a diameter smaller than a diameter of the passage.

15. The method according to claim 14, wherein the main housing comprises a linear, flat skin contact side or a curved skin contact side.

* * * * *